US00PP34740P2

(12) United States Plant Patent
Wood

(10) Patent No.: US PP34,740 P2
(45) Date of Patent: Nov. 15, 2022

(54) ***HYDRANGEA* PLANT NAMED 'SMHPS'**

(50) Latin Name: *Hydrangea paniculata*
Varietal Denomination: SMHPS

(71) Applicant: Spring Meadow Nursery, Inc., Grand Haven, MI (US)

(72) Inventor: Timothy D. Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/839,816

(22) Filed: Jun. 14, 2022

(51) Int. Cl.
*A01H 5/00* (2018.01)
*A01H 6/48* (2018.01)

(52) U.S. Cl.
USPC ..... Plt./250

(58) Field of Classification Search
None
See application file for complete search history.

*Primary Examiner* — Susan McCormick Ewoldt
(74) *Attorney, Agent, or Firm* — Cassandra Bright

(57) ABSTRACT

A new and distinct cultivar of *Hydrangea* plant named 'SMHPS' is disclosed, characterized by lace-cap inflorescences with bright pinkish-red sepals in late summer to fall. Plants have dwarf habits, dark green foliage, and strong, upright stems. The new variety is a *Hydrangea*, typically produced as an outdoor ornamental plant.

2 Drawing Sheets

Latin name of the genus and species: *Hydrangea paniculata.*

Variety denomination: 'SMHPS'.

BACKGROUND OF THE INVENTION

The new cultivar is a product of a planned breeding program conducted by the inventor, at a commercial nursery in Grand Haven, Mich. The objective of the breeding program was to produce new *Hydrangea* varieties with dwarf habits, good health and vigor, and attractive blooms. The open-pollination resulting in the new variety was made during 2007.

The seed parent cannot be identified, as it is from bulked seed from early flowering selections of unnamed, unpatented dwarf *Hydrangea paniculata* varieties. The pollen parent cannot be identified as this new selection resulted from an open-pollination.

The new variety was found and selected by the inventor in 2011 at the same nursery in Grand Haven, Mich.

Asexual reproduction of the new cultivar 'SMHPS' was first performed during 2011 in Grand Haven, Mich., by softwood cuttings. Through subsequent propagation, multiple additional generations have been reproduced, having shown that the unique features of this cultivar are stable and reproduced true to type.

SUMMARY OF THE INVENTION

The cultivar 'SMHPS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMHPS'. These characteristics in combination distinguish 'SMHPS' as a new and distinct *Hydrangea* cultivar:

1. Dwarf, compact habit.
2. Strong, upright stems.
3. Thick, strong leaves with a coarse texture.
4. Dark green foliage.
5. Lace-cap inflorescences.
6. Bright pinkish-red late summer to fall color to sepals.

PARENT COMPARISON

Parent comparisons for *Hydrangea* 'SMHPS' are unavailable, as both parents are unidentified.

COMMERCIAL COMPARISON

Plants of the new cultivar *Hydrangea* 'SMHPS' can be compared to the commercial variety *Hydrangea* 'SMNHPK', U.S. Plant Pat. No. 32,512. Plants of 'SMHPS' are similar to plants of 'SMNHPK' in most horticultural characteristics, however, plants of 'SMHPS' differ in the following:

1. 'SMHPS' has thicker, more coarsely textured leaves than 'SMNHPK'.
2. 'SMHPS' has broad leaves with small tips, while 'SMNHPK' has narrow elliptical leaves with prominently acuminate tips.
3. 'SMHPS' has lace-cap inflorescences, while 'SMNHPK' has mop-head inflorescences.
4. 'SMHPS' has a very upright habit, while 'SMNHPK' has a less upright habit.

BRIEF DESCRIPTION OF THE PHOTOGRAPHS

Figure 1:
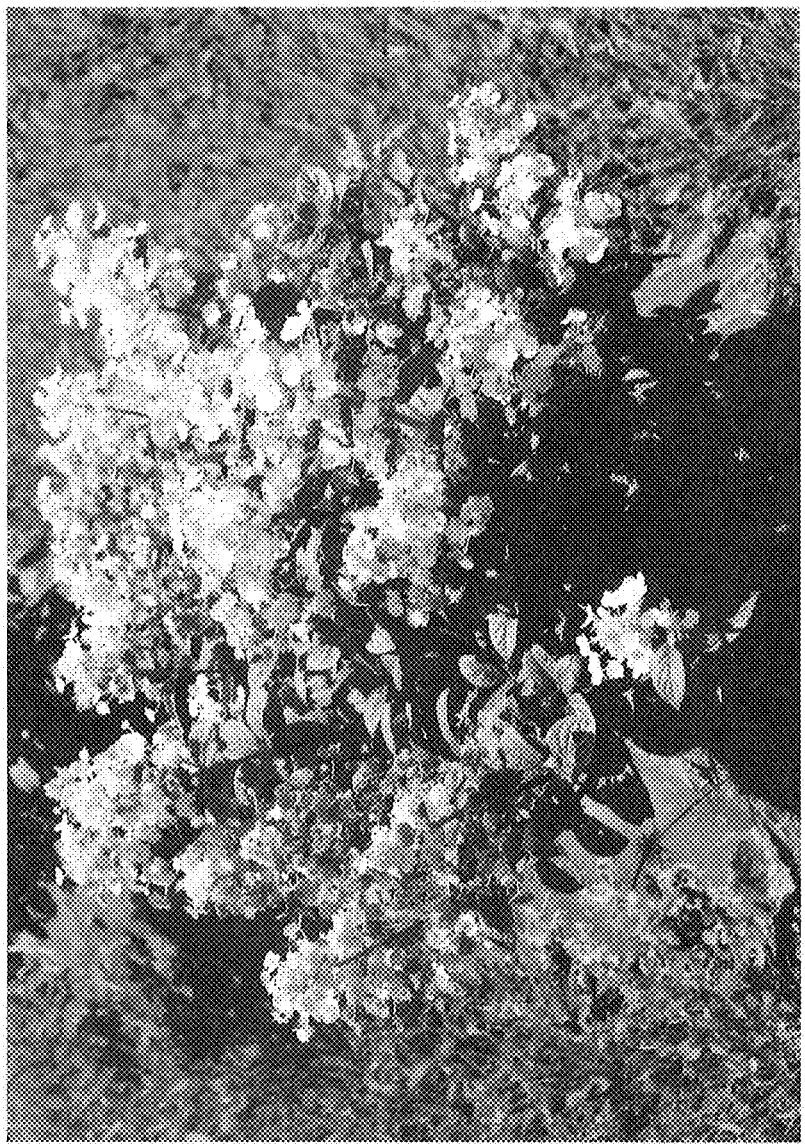

The accompanying photograph in FIG. 1 illustrates in full color a typical plant of 'SMHPS' grown outdoors in Grand Haven, Mich. This plant is approximately 2-3 years old, grown in a 3-gallon container during late Spring.

Figure 2:
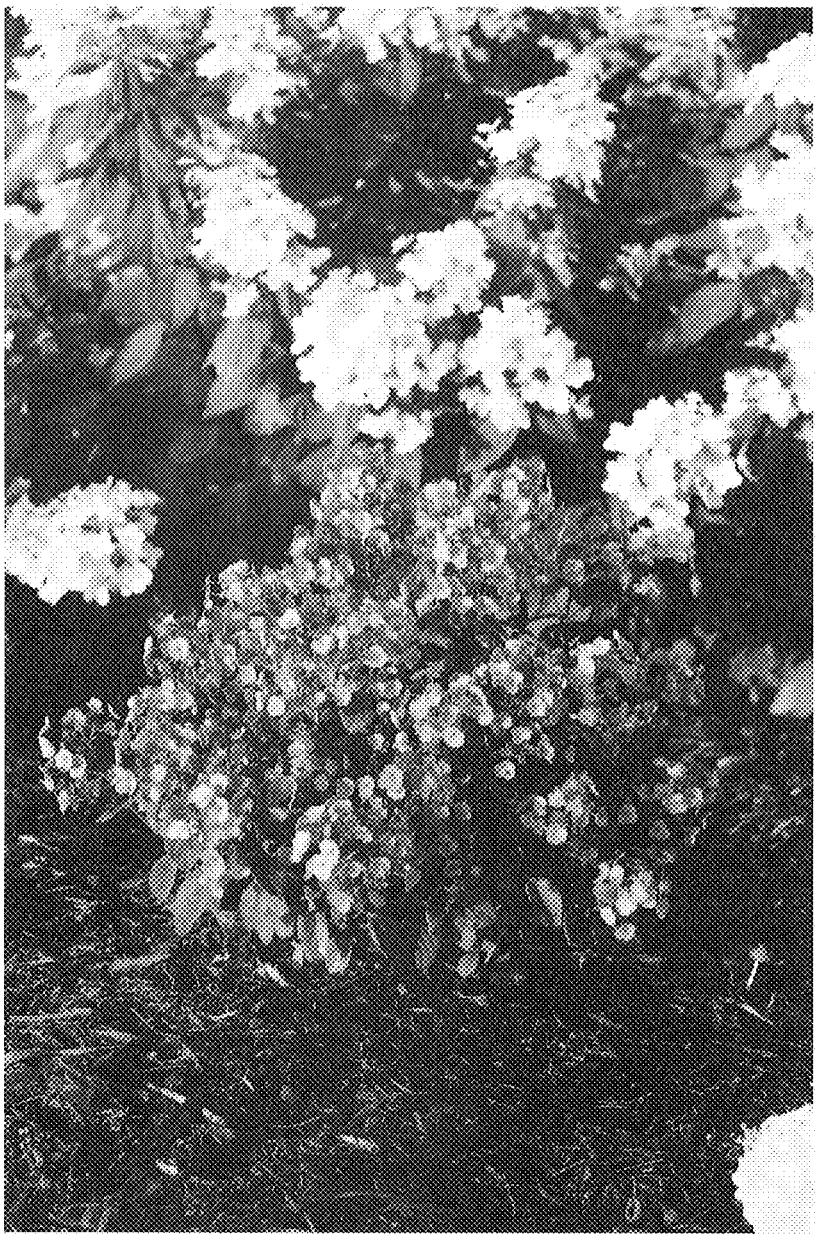

FIG. 2 illustrates in full color a plant of 'SMHPS' during early Fall, with darker sepal coloration.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMHPS' plants grown outdoors in Grand Haven, Mich. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea paniculata* 'SMHPS'.

PROPAGATION

Typical method: Softwood cuttings.
Root initiation: Approximately 18 days.
Time to produce rooted cutting: 60 days during summer.
Roots: Thick to thin, freely branching, fibrous, dense. White to brown in color, not accurately measured with R.H.S. chart.

PLANT

Plant shape: Quite upright.
Growth habit: Mostly upwards.
Height: 50 cm.
Plant spread: 35 cm.
Pot size of plant described: #3 container.
Age of plant described: Approximately 2 to 3 years.
Growth rate: Slow to moderate.
Plant vigor: Good.
Stem:
- *Branching*.—Basal.
- *Number of lateral branches*.—8 to 10.
- *Shape*.—Rounded.
- *Color*.—Immature: RHS Yellow-Green N144D. Mature: RHS Yellow-Green N144D with tinges of Greyed-Orange 176A, and Yellow-Green 145D lenticels. Old growth: RHS Greyed-Brown N199B.
- *Length*.—45 cm.
- *Width*.—1 cm.
- *Aspect*.—60 to 80°.
- *Strength*.—Strong.
- *Pubescence*.—None.
- *Internode length*.—4 to 5 cm.

FOLIAGE

Leaf:
- *Arrangement*.—Opposite.
- *Shape*.—Elliptical.
- *Length*.—9 cm.
- *Width*.—6.5 cm.
- *Apex*.—Acuminate.
- *Base*.—Obtuse.
- *Margin*.—Very slightly serrulate.
- *Texture of top surface*.—Coarse, with fine hairs and pronounced venation.
- *Texture of bottom surface*.—Coarse, with fine hairs along veins and mid-rib.
- *Pubescence*.—On both sides.
- *Color*.—Young foliage upper side: Near RHS Yellow-Green 146A. Young foliage under side: Near RHS Yellow-Green 146B. Mature foliage upper side: RHS Green NN137B. Mature foliage, under side: Near RHS Greyed-Green 191B.

Venation:
- *Type*.—Pinnate.
- *Color*.—Upper side: RHS Yellow-Green N144D with tinges of Greyed-Orange 176A. Under side: Near RHS Greyed-Green 191B.

Petiole:
- *Length*.—2 cm.
- *Width*.—4 mm.
- *Color*.—Upper side: RHS Yellow-Green N144D, with tinges of Greyed-Orange 176A. Under side: RHS Yellow-Green N144D, with tinges of Greyed-Orange 176A.
- *Texture*.—Upper side: Very slight pubescence. Under side: Very slight pubescence.

INFLORESCENCE

Natural flowering season: Summer.
Inflorescence type: Lace-cap.
Panicle:
- *Shape*.—Upright, cone-shaped, rounded.
- *Height*.—10 cm.
- *Diameter*.—8 cm.

Fragrance: None.
Sterile flowers:
- *Flowers per inflorescence*.—40 to 50.
- *Aspect*.—Upright.
- *Shape*.—Round whorl.
- *Length*.—2.5 cm.
- *Diameter*.—2.5 cm.
- *Depth*.—5 mm.
- *Persistent or self-cleaning*.—Persistent.

Bud:
- *Length*.—3 mm.
- *Bud diameter*.—3 mm.
- *Bud shape*.—Elliptic, obovate.
- *Bud color*.—RHS Green-White 157A.

Petals:
- *Number per flower*.—4.
- *Arrangement*.—Stellate.
- *Shape*.—Elliptic.
- *Tip*.—Acute.
- *Base*.—Flat.
- *Margin*.—Entire.
- *Length*.—3 mm.
- *Width*.—2 mm.
- *Texture*.—Upper side: Smooth, soft. Under side: Smooth, soft.
- *Color*.—When Opening, Upper side: RHS White NN155A. When Opening, Under side: RHS White NN155A. Fully Opened, Upper side: RHS White NN155A. Fully Opened, Under side: RHS White NN155A.

Sepal:
- *Number*.—4.
- *Arrangement*.—Cruciform.
- *Shape*.—Reniform.

*Tip*.—Emarginate.
*Base*.—Truncate.
*Margin*.—Entire.
*Length*.—12 mm.
*Width*.—2 cm.
*Texture*.—Upper side: Smooth and soft with some pronounced venation. Under side: Smooth and soft with some pronounced venation.
*Color*.—When Opening, Upper side: RHS Green-Yellow 1D, with tinges of Green-Yellow 1C. When Opening, Under side: RHS Green-Yellow 1D, with tinges of Green-Yellow 1C. Fully Opened, Upper side: RHS White 155A. Fully Opened, Under side: RHS White 155A. Fading, Upper side: RHS Red-Purple 63A. Fading, Under side: RHS Red-Purple 63A.

Pedicle:
*Length*.—2 cm.
*Diameter*.—2 mm.
*Angle*.—45°.
*Strength*.—Good, flexible.
*Texture*.—Lightly pubescent.
*Color*.—RHS White 155A.

Fertile flowers:
*Flowers per inflorescence*.—300 to 400.
*Aspect*.—Upright.
*Shape*.—Stellate.
*Length*.—6 mm.
*Diameter*.—6 mm.
*Depth*.—4 mm.
*Persistent or self-cleaning*.—Self-cleaning.

Bud:
*Length*.—3 mm.
*Bud diameter*.—3 mm.
*Bud shape*.—Elliptic, obovate.
*Bud color*.—RHS Green-White 157A.

Petals:
*Number per flower*.—5.
*Arrangement*.—Stellate.
*Shape*.—Elliptic.
*Tip*.—Acute.
*Base*.—Flat.
*Margin*.—Entire.
*Length*.—3 mm.
*Width*.—2 mm.
*Texture*.—Upper side: Smooth, soft. Under side: Smooth, soft.
*Color*.—When Opening, Upper side: RHS White NN155A. When Opening, Under side: RHS White NN155A. Fully Opened, Upper side: RHS White NN155A. Fully Opened, Under side: RHS White NN155A.

Sepal: None.

Pedicle:
*Length*.—2 mm.
*Diameter*.—1 mm.
*Angle*.—45°.
*Strength*.—Good.
*Texture*.—Smooth.
*Color*.—RHS White NN155A.

REPRODUCTIVE ORGANS

Sterile flower:
Stamens:
*Number*.—10.
*Filament color*.—RHS White NN155B.
*Filament length*.—3 mm.
Anthers:
*Length*.—>1 mm.
*Shape*.—Rounded, basifixed.
*Color*.—RHS Yellow-White 158B.
*Pollen*.—Good amount.
*Pollen color*.—RHS Yellow-White 158B.
Pistil:
*Number*.—1.
*Length*.—2 mm.
Stigma:
*Shape*.—3-lobed.
*Color*.—RHS Green-White 157D.
*Style length*.—1 mm.
*Style color*.—RHS Green-White 157D.
*Ovary color*.—RHS Green-White 157D.

Fertile flower:
Stamen:
*Number*.—10.
*Filament length*.—3 mm.
*Filament color*.—RHS White NN155B.
Anther:
*Shape*.—Rounded, basifixed
*Length*.—>1 mm.
*Color*.—RHS Yellow-White 158B.
*Pollen amount*.—Good.
*Pollen color*.—RHS Yellow-White 158B.
Pistil:
*Number*.—1.
*Length*.—2 mm.
Stigma:
*Shape*.—3-lobed.
*Color*.—RHS Green-White 157D.
*Style length*.—1 mm.
*Style color*.—RHS Green-White 157D.
*Ovary color*.—RHS Green-White 157D.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −32° C. and tolerates an upper temperature range to at least 36° C.

Fruit/seed production: Not observed to date.

What is claimed is:

1. A new and distinct cultivar of *Hydrangea* plant named 'SMHPS' as herein illustrated and described.

* * * * *